United States Patent [19]

Hall

[11] 4,284,076
[45] Aug. 18, 1981

[54] NASO-GASTRIC TUBE STABILIZER
[75] Inventor: Richard Hall, New Canaan, Conn.
[73] Assignee: Technalytics, Inc., Upper Saddle River, N.J.
[21] Appl. No.: 152,593
[22] Filed: May 23, 1980
[51] Int. Cl.³ ............................................. A61M 25/02
[52] U.S. Cl. ........................ 128/207.18; 128/DIG. 26
[58] Field of Search ........................ 128/207.18, 207.14, 128/207.15, 207.16, 348, 349 R, 349 B, 349 BV, 350 R, 350 V, DIG. 26, 3, 4, 12, 15, 342, 343

[56] References Cited
U.S. PATENT DOCUMENTS

| 2,245,969 | 6/1941 | Francisco et al. | 128/207.18 |
| 2,586,940 | 2/1952 | Graham | 128/DIG. 26 |
| 3,059,645 | 10/1962 | Hasbrouck et al. | 128/DIG. 26 |
| 3,814,080 | 6/1974 | Norman | 128/DIG. 26 |
| 3,972,321 | 8/1976 | Proctor | 128/207.18 |
| 4,170,995 | 10/1979 | Levine et al. | 128/DIG. 26 |

FOREIGN PATENT DOCUMENTS 653436 5/1936 Fed. Rep. of Germany ... 128/DIG. 26

Primary Examiner—Henry J. Recla
Attorney, Agent, or Firm—J. David Dainow

[57] ABSTRACT

A naso-gastric tube stabilizer device having a base part, a harness for releasably holding the device on a patient's head, and a spring member secured for releasably securing to the device an exposed section of a naso-gastric tube extending out of the patient's nostril.

10 Claims, 10 Drawing Figures

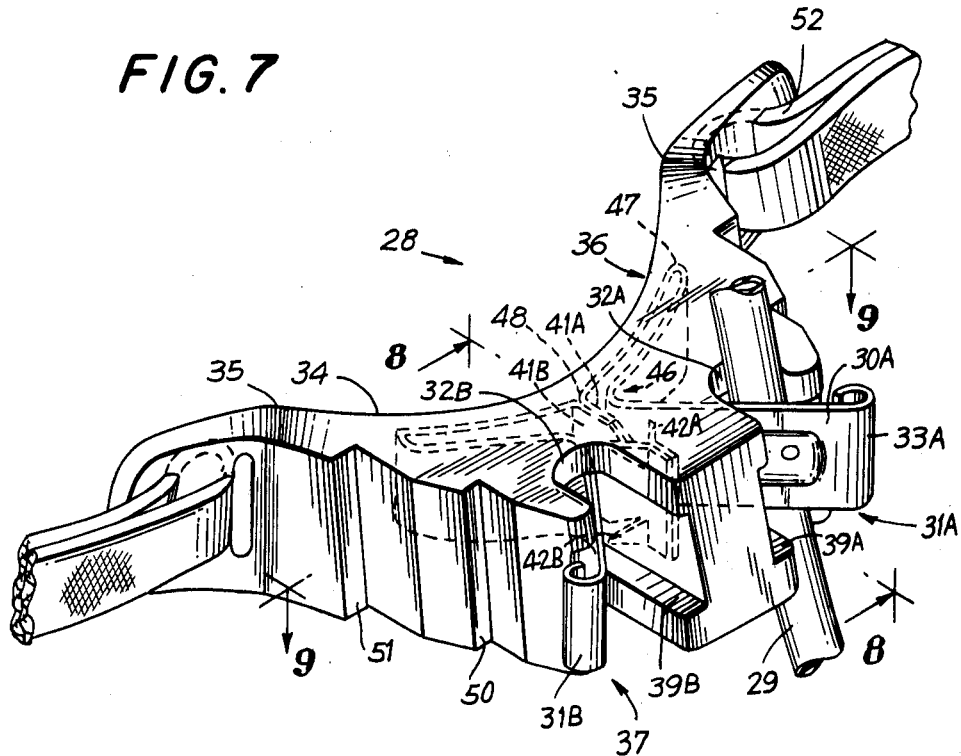
FIG. 7
FIG. 8
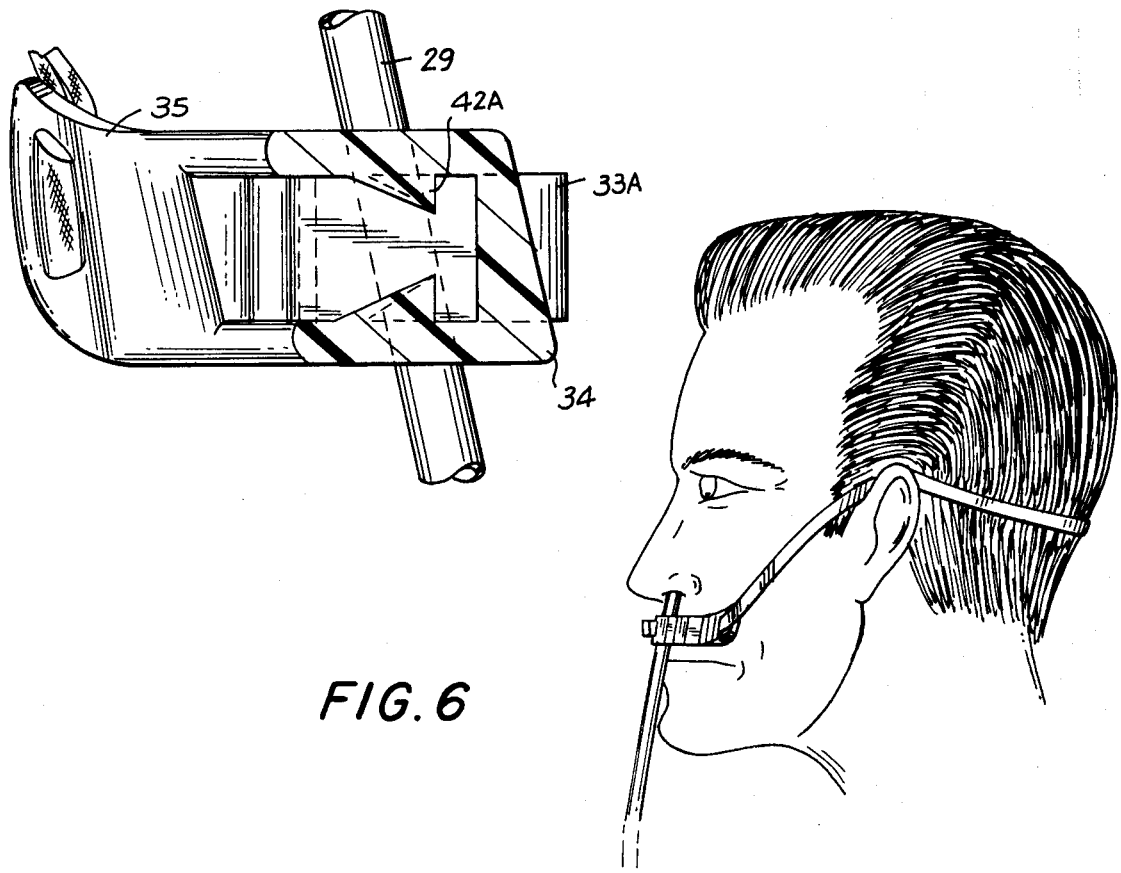
FIG. 6

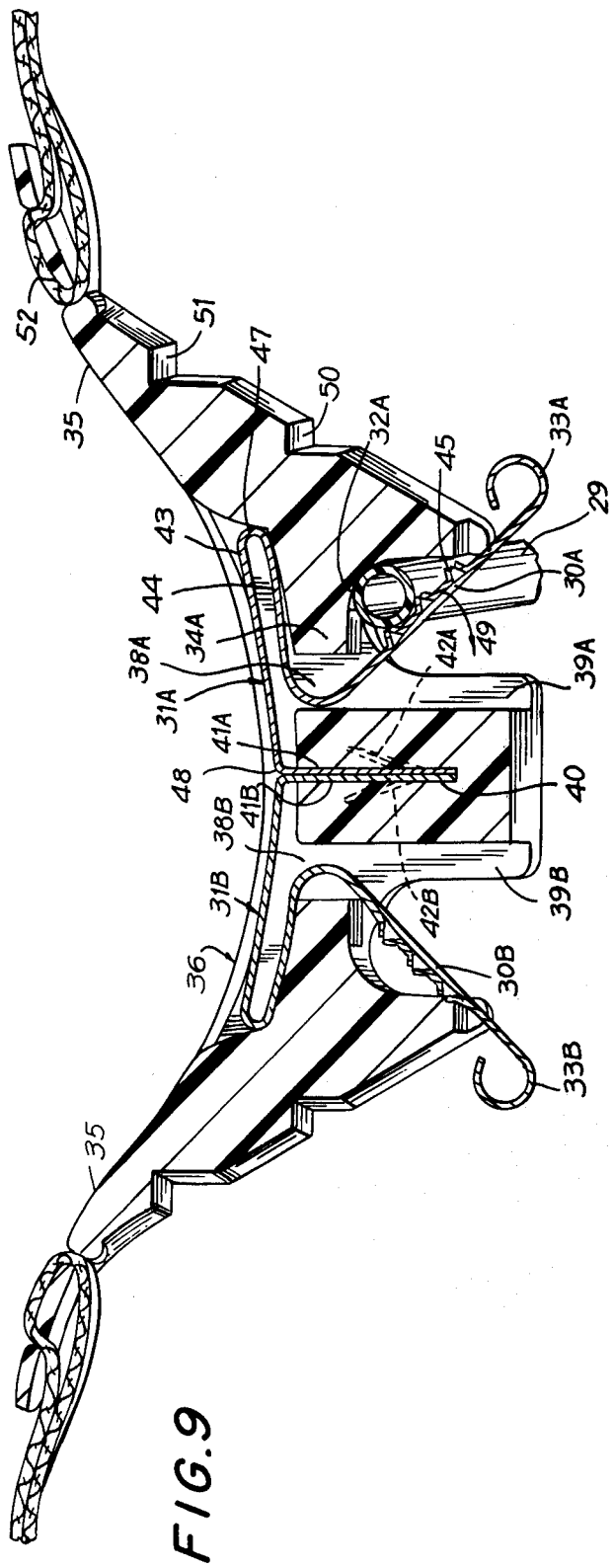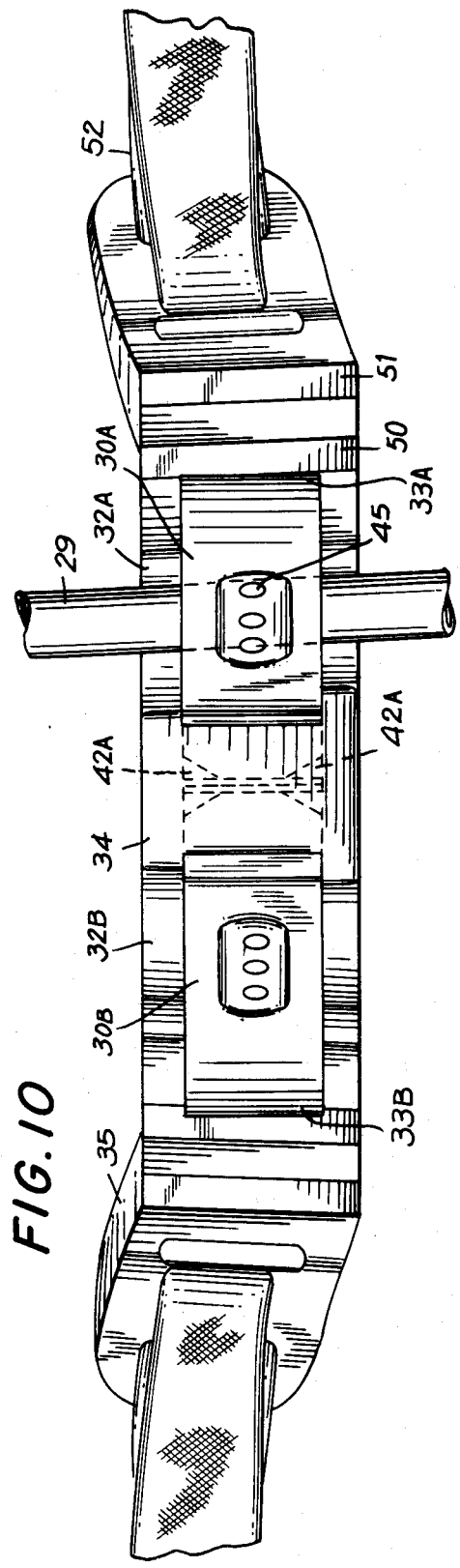

NASO-GASTRIC TUBE STABILIZER

BACKGROUND OF THE INVENTION

This invention is in the field of naso-gastric tubes or stomach tubes, which are commonly used devices during and following surgery. This type of tube is typically made of clear or tinted plastic having proximal and distal ends, a central bore and additional apertures near the distal end. In use the distal end is inserted upward into a patient's nostril or mouth; then it is pushed along a path past the nasal pharynx, then downward past the oral pharynx, and finally downward through the esophagus into the stomach. At the proximal end a suction pump is connected for drainage of gastric secretions, particularly when a patient is being fed intravenously. These tubes or catheters typically remain in place from several hours to two weeks depending on the patient's condition, this device and procedure being essentially unchanged in approximately forty years. Of course there have been developed improved plastic materials which produce tubes which are stronger, smoother, self-lubricating, have x-ray opaque markings for fluoroscopic location during and after insertion, and are designed to reduce clogging.

These tubes, now made by more than one dozen manufacturers, are generally successful for their primary purpose, namely reliable drainage. However, there are numerous unpleasant, uncomfortable and sometimes dangerous ancillary effects associated with the use of these tubes or catheters, certain of these negative aspects being so familiar to surgeons and nursing staff that they have become accepted as inherent parts of procedures which require the use of naso-gastric tubes. There are two different types of problems with which we are presently concerned: (a) actual irritation, necrosis and/or ulceration of tissue associated with the nostril, pharynx, and esophagus, and (b) painful discomfort to these areas, often becoming sheer misery for the patients who must experience an indwelling naso-gastric tube or catheter during their stay in a hospital.

Certain of the problems and discomfort described above are inherent in the procedure of inserting and maintaining a naso-gastric tube in a patient's nostril; however, thereafter these problems can become aggravated by (a) bending and twisting of the otherwise stationary indwelling tube, (b) by gross movement of the tube or the patient relative to the tube, and (c) by the well-known and standard technique of using layers of adhesive tape to secure the exposed portion of the tube to the patient's upper lip or nose and cheek. Bending and twisting of the indwelling tube occurs because the downward extending exposed portion of the tube near the upper lip is bent and the tube is redirected upward past the cheek and thence to a suction apparatus. While the tube feels somewhat soft, this is misleading. In reality the tube has considerable stiffness so that it will not collapse inwardly due to the suction, and will not collapse or bend transverse to its axis while it is being pushed axially during insertion about numerous and reverse curves of the internal passageways. Thus the tube has considerable hardness and any portion of the tube bearing against tissue can lead to great pain.

Another important but subtle problem is the reaction force set up by bending this "apparently soft" tube as it exits the nostril. The edge of the nostril or other point of contact by the tube becomes a fulcrum or pivot point contacted by an intermediate portion of the tube between a lower exposed portion of the tube which is bent or pulled, and an upper indwelling portion. Specifically, if the lower part is pulled to the right, the intermediate portion remains in contact where it was, and the inward portion tends to move to the left and produce a reaction force to the left against adjacent tissue. It has been determined that this reaction force may be quite substantial.

The second of three above-listed aggravating factors in causing pain and necrosis is gross movement of the tube or the patient, as contrasted with bending and twisting a stationary tube. The tube extending out of a nostril can be moved or even yanked when the patient moves in certain improper ways, or when the sheet or other apparatus to which the tube is attached is improperly moved, or even from coughing or swallowing by the patient, with a result of severe pain in the nostril and adjacent areas.

The use of adhesive tape to reduce tube movement is only partially successful for that purpose, and such tape creates new and sometimes worse problems. The tape itself is unpleasant in that it pulls the skin constantly, is particularly uncomfortable in hot, humid conditions, and is painful to remove from the skin. Removal of the tape from the tube, when necessary, causes additional movement of the tube and associated pain. Another particularly unfortunate feature of using adhesive tape is that the tape typically holds the tube closely and tightly against the upper lip or philtrum; however, the natural direction of the tube upon exiting the nose is outward, away from the upper lip surface, and this act of adhering the tube to that surface is effectively bending the tube and causing a reaction force against other tissue upward in the nostril, as described earlier. The prior art use of additional adhesive tape to hold a portion of the naso-gastric tube tightly against the patient's cheek, leads to further pulling of the skin and bending the tube into an unnatural curvature with associated reaction forces.

Certain devices have been proposed in the prior art which engage an exposed portion of a naso-gastric tube by means of adhesive or elastic tape, or use of a sleeve or collar about the tube, while the device is secured to the head by separate tape or a harness encircling the head. This use of tape in prior devices is now considered undesirable because of the time and nuisance to secure and release the tape and the loss of effectiveness when the tape becomes wet; any requirement for wrapping elastic around the tube or sliding a collar along the length of the tube extending out of the patient's nostril either causes pain which the present invention seeks to avoid, or is too clumsy and impractical to be taken seriously. In one case a spectacle-type frame was proposed which included a clip on one temple for engaging a portion of the nasal catheter, but made no effort to align the tube properly or to prevent movement of the tube in the vicinity of the nostril. In still another unsuccessful attempt to truly solve the problems described above, an adhesive-backed VELCRO patch was adhered to the patient's cheek, and a collar with a VELCRO outer surface is secured on the tube. When pressed together the mating VELCRO surfaces will releasably adhere together; however emplacement of the collar on the tube is impractical, and the use of adhesive on the face is a procedure the present invention successfully avoids. A still further attempt to solve the above-described problems involved a device which engaged and aligned the exposed portion of a naso-gastric tube by means of slots and grooves; however, in order for the device to have sufficient strength and resilience to securely but releasably grip the tube without additional holding means, the device was made of semi-rigid material and therefore was relatively hard, and when pressed against the patient's upper lip during use, produced its own discomfort.

In reviewing all the known prior art, none of the devices solve all the problems inherent with naso-gastric tubes and inherent with the devices themselves intended to releasably locate and secure these tubes. The present invention is a device and technique which finally combine structural features to align and securely and releasably grip the tube with ease and speed, while vastly reducing patient discomfort without introducing new discomfort. More particularly, this new invention successfully reduces irritation necrosis, ulceration and pain caused by indwelling naso-gastric and related tubes, as is summarized below, followed by a detailed description of preferred embodiments of the new concept.

SUMMARY OF THE INVENTION

This invention is a device and technique for engaging a naso-gastric or other tube where it exits a patient's nose, and stabilizing the tube as regards movement in all directions. By this stabilization the tube is restrained from moving (a) axially or lengthwise further into or out of the nostril, (b) laterally toward the sides of the nostril, (c) depthwise toward the front or rear of the nose, (d) angularly by changing orientation within the nose, and (e) rotatably about its longitudinal axis. The device also reduces reaction force caused by an indwelling portion of the tube beyond the portion of the tube which is actually engaged.

In a preferred embodiment the device engages the tube in a secure but readily releasable manner, by providing a resilient gripping means which is deflectable between a first position to expose a guide surface for engaging and aligning the tube, and a second position urging the tube against the guide surface. In addition to the device gripping the tube, the device itself and captured tube are secured from moving relative to the patient's head by a harness means extending from edges of the device near the upper lip, past the cheeks, to the rear of the head or neck. The harness is of course adjustable in length and tension, to avoid creating new pressure discomfort while still holding the device and tube securely.

Another feature of the new device is its ability to grip the tube while essentially not changing the tube's natural orientation upon exiting the nose; thus we are able to greatly reduce the bending, twisting and/or pulling of the tube in the area where it exits the nose, and inward thereof where irritation and discomfort tend to be extreme with prior art naso-gastric tubes. More particularly, the preferred device allows the tube, while it extends generally downward, to remain in its normal orientation of being angled slightly sideward, toward the left cheek from the left nostril for example, and slightly forward away from the mouth, even though the remainder or proximal portion of the tube is actually redirected in an upward and lateral direction past the cheek.

A still further feature of this invention is a clip carried by the harness and situated near the patient's cheek. The clip is adapted to engage and releasably hold the portion of the tube directed past the cheek, so that adhesive tape for holding the tube to the cheek can be eliminated. In preferred embodiments the clip is pivotable, so that the tube, though gripped, can find or retain its natural orientation; this avoids one more imposed and unnatural bend in the tube and thus further reduces the sources of patient discomfort.

The device itself may take various forms within the scope of this invention, but preferably it is a soft, flexible and easily pliant material formed as a curved arch or central section having a concave surface for placement against the patient's upper lip, a front portion where a tube is releasably engaged, and means at the two ends of the central part for engaging a harness. On the front surface are one or two guide areas for receiving and properly aligning the exposed portion of the tube to coincide generally with the axis of the nostril from which the tube extends. The guide areas are dimensioned to receive a naso-gastric (sometimes abbreviated "NG") tube having diameter designated 12, 14, 16 or 18 French; a resilient means such as a separate spring cooperates with the guide area to secure the tube as so aligned, or to independently, releasably engage the tube. The act of engaging the tube along a section of defined length is an improvement over one prior art technique of gripping the tube at a single axial location which functions as a fulcrum allowing the tube to be bent above or below the fulcrum which produces an opposite reaction force in the portion of the tube beyond the fulcrum.

The central section of the base may be thicker to add firmness, however the material of the base including its ends or wings is soft and totally comfortable to the user. The material of the base may also be selected to be essentially the same as certain naso-gastric tubes made of polyvinylchloride; this will result in a very high coefficient of friction between the device and the tube which enhances the overall stabilization of the tube.

This movable spring may have exposed gripping means which are easily actuated by the patient's doctor or nurse. The movable portion of the spring that contacts the NG tube may have sharp projections that slightly pierce the surface of the tube, or at least distort the tube surface sufficiently to create a mechanical and/or frictional grip upon such surface. The NG tube has a smooth, hard, slippery surface for medical reasons, for strength requirements, and to allow easy passage through the internal body passages, and it is because of these surface characteristics that the tube-gripping means have a difficult task. Even bending the tube around obstacles helps to create mechanical and/or frictional gripping. Finally, the movable spring element can be replaced by a semi-rigid gripping element that is movable between a first position that exposes a bearing surface to receive the tube and a second position where the gripping element secures the tube in place.

As indicated above the various embodiments within the scope of this invention demonstrate the feasibility for stabilizing a naso-gastric tube in a manner which effectively reduces irritation and pain that have been almost universal problems for patients who are subjected to these indwelling naso-gastric and other tubes. Additional features of the preferred embodiment will be described below in conjunction with the drawings as follows.

BRIEF DESCRIPTION OF THE DRAWINGS

FIG. 6 is a side view of the naso-gastric tube stabilizer device positioned on a patient's head;

FIG. 7 is a front perspective view of the new device;

FIG. 8 is a cross-sectional view taken along lines 8—8 in FIG. 7;

FIG. 9 is a sectional view taken along lines 9—9 of FIG. 7; and

FIG. 10 is a front elevation view of the device in FIG. 7;

DETAILED DESCRIPTION OF THE PREFERRED EMBODIMENT

Figure 1:
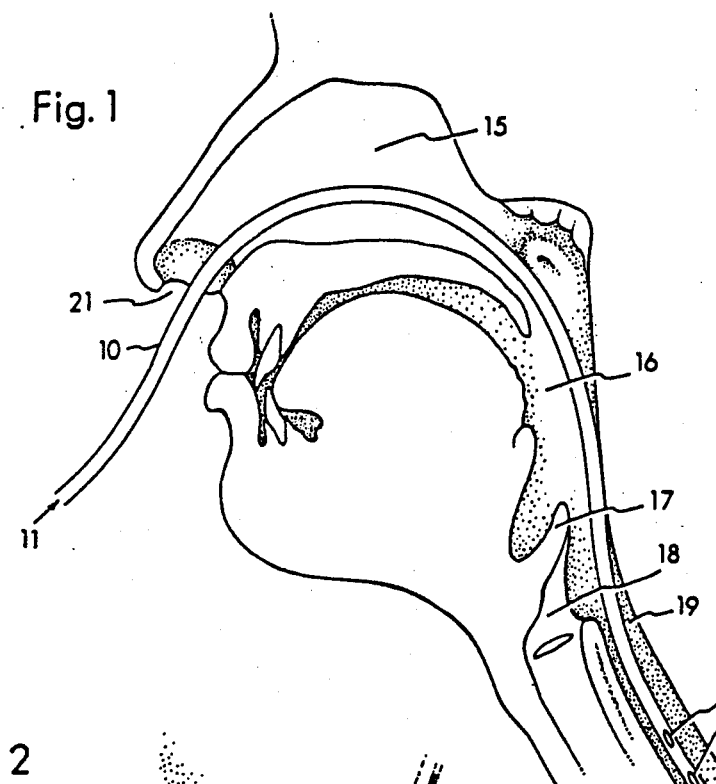
FIG. 1 is a partial mid-sagittal sectional view of a person's head.

FIG. 1 shows a cross-section of a patient's head with a naso-gastric tube inserted in the normal fashion. The tube 10 has a proximal end 11 which leads to suctioning apparatus and a distal end 12, with a bore through the entire length of the tube which terminates as opening 13 and communicates with additional openings 14 at the distal end which is pushed all the way into the lowest area of the stomach. At the time of insertion the distal end starts in through the nostril at 21 and moves into area 15 designated nasal pharynx, then past areas 16 and 17 and 18 designated oral pharynx, epiglottis, and orifice to the trachea, respectively, and finally into the passage 19 leading to the esophagus.

Figure 2:
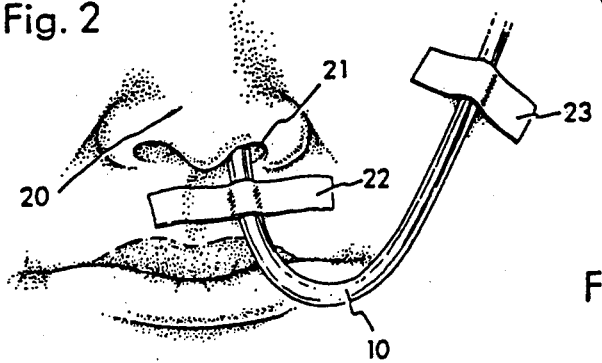
FIG. 2 is a fragmentary front elevation view of a person's face, showing a naso-gastric tube in place.
Figure 3:
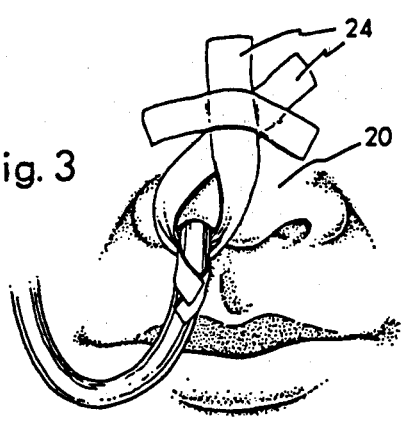
FIG. 3 is a view similar to that of FIG. 2.

FIG. 2 shows a front view of a patient's nose 20 with the tube 10 extending outward through a nostril marked 21, then upward leading to suctioning apparatus. Typically in the prior art, the tube 10 is maintained in place by adhesive tape 22 which may be secured to the patient's upper lip, and/or additional tape 23 secured to the patient's cheek. Another prior art adhesive tape technique as shown in FIG. 3, comprises the use of one or more strips of tape 24 from the top surface of the nose 20 downward to the portion of the tube extending out of the nose.

The adhesive tape causes general discomfort whereever it is used, and further discomfort if the tube is caused to move for one of numerous possible reasons and the tape pulls on the skin wherever it happens to be attached. There are a variety of reasons why the tube might be pulled, including mere movement of the patient relative to the proximal end, which is in the suction means, or having something touch or push the tube, such as the patient's hand or clothing, or movement of the patient's head while the rest of his body remains still. Finally some movement of the tube may occur due to swallowing or breathing, coughing or sneezing by the patient.

A second form of discomfort and irritation caused by the tube, whether it moves or not, is pressure contact of the tube against various tissues. As can be seen, the naso-gastric tube is a bendable plastic tube which must be flexible enough to conform to the varying shapes of the passages into which it is inserted, and no two passages will be identical. The tube must also have sufficient rigidity, so that it will not collapse about a transverse axis when it is pushed axially and urged to follow the passage, and will not collapse radially when suction is applied. Consequently, it can be seen that portions of this semi-rigid tube will, where they contact portions of the body, apply some kind of pressure, which may cause actual pain, or may irritate without the patient being initially aware, leading to later tenderness or actual lesions and/or scarring. This is indicated, for example, in FIG. 4 where the tube 10 contacts the lateral edge 25 of the nostril, and where an inward portion 26 of the tube contacts the lateral wall of the medial septum.

Figure 4:
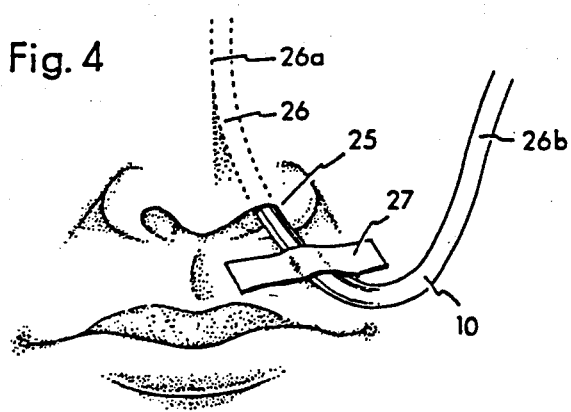
FIG. 4 is another view similar to that of FIG. 2.
Figure 5:
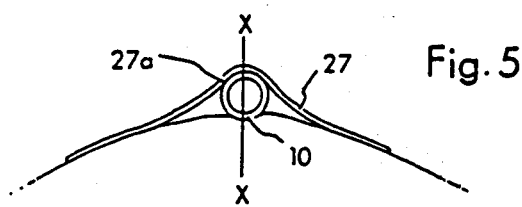
FIG. 5 is a sectional view through a naso-gastric tube adhered to a patient's face with adhesive tape.

Lateral pressure contact by part 26a of the tube, indicated in FIG. 4, is made more severe by reaction forces resulting from bending adjacent part 26b of the tube. Between parts 26a and 26b the tube is held by adhesive tape 27 which tends to operate as a fulcrum point. The tape is effective to generally hold the tube in place, however in FIG. 5, point 27a points to the very small area of actual contact of the tape 27 on the tube 10. Thus the tape restrains the tube from gross movements axially or laterally, but in actual use the portion of the tube under the tape does pivot about an axis x—x shown in FIG. 5.

The new invention illustrated in FIGS. 6-10 provides a device which will greatly reduce the above-described pivoting movement or random movement of the tube once it is placed, will reduce pressure contact in areas where discomfort occurs, will reduce discomfort on the upper lip or cheek tissue caused by adhesive, and will reduce the compounded discomfort due to pulling of the adhesive when that occurs. In FIGS. 7-10 a butterfly-type naso-gastric tube stabilizer device 28 is shown with a segment of tubing 29 representing a naso-gastric tube captured in this device between arm 30A of a first spring 31A and trough 32A. A second similar spring 31B is positioned adjacent to spring 31A but flipped over 180°. This device comprises a base or central part 34 and wings 35, all being a one-piece injection molded product. For various reasons discussed later, a preferred embodiment of this base part is made from a relatively soft and flexible polyvinylchloride.

The device of FIGS. 7-10 is used as illustrated in FIG. 6 by placing the rear surface 36 against a patient's upper lip or philtrum, releasable securing an exposed portion of a naso-gastric tube onto the device, and releasably securing the device onto the patient's head. As shown in the Figures the device has two troughs 32A and 32B extending from top to bottom on the front surface 37; these troughs diverge in the downward direction, and are spaced apart and angled so that a tube in a trough would be generally aligned with the axis of the corresponding nostril. Accordingly, when the exposed portion of an NG tube is secured in one of these troughs, the unexposed portion within the nasal passage remains generally aligned and unbent relative to the exposed portion, which substantially reduces the tendency of this tube to rub against and irritate sensitive tissues in the nasal passage and at its opening adjacent the upper lip. Also note each trough is angled from the upper front surface downward and further forward away from the rear surface, which completes the alignment step in positioning the troughs.

The device as a whole and particularly its rear surface is relatively soft and flexible to facilitate its conforming to the contours of the patient's upper lip and cheeks, and to thereby avoid applying pressure contact on these surfaces by any hard or sharp part of the device. Soft polyvinyl-chloride is used for a preferred embodiment of the invention for the comfort it provides to the patient and for a second reason. Many typical NG tubes are also made of polyvinyl-chloride having and extremely tough and slippery surface, which leads to difficulties in firmly gripping and securing the tube to the NG stabilizer device. It has been discovered that by forming the device of essentially the same or similar material as the tube, a rather large frictional resistance will develop between the tube and device when they are urged together. Thus, if the tube is pressed against the trough, their circumferential surfaces will be in pressure contact, and it will be difficult to slide one relative to the other. The requirement therefore is to provide releasable means for urging the tube against a trough, and this has been accomplished by the spring members 31A and 31B which are separate elements that cooperate together.

As mentioned above, the two springs 31A and 31B have essentially the same configuration, but one is flipped 180° relative to the other. For convenience only one spring will be fully described in detail, except for an explanation of how these springs cooperate to produce a result that neither one could produce alone. First note that there are two apertures 38A, 38B which extend completely through the base 34 from rear to front, and front recesses 39A, 39B which overlie these apertures respectively. Between apertures 38A, 38B is a central slot 40 (FIG. 9) that extends from the rear side 36 in a forward direction only partially through base 34.

Spring 30A has an anchor part 41A (see FIGS. 7–10), upper and lower tangs 42A, a U-shaped central part formed by rear wall 43 and front wall 44, arm 30A, jagged projections 45 formed by piercing the arm, and rounded tip 33A. Each tang 42A is a resilient element that normally flares outward at the angle shown, but is displaceable to lie generally in the plane of the anchor part 41A.

As shown in the Figures the springs are positioned with their anchor parts 41A, 41B adjacent, bearing against each other, and fully inserted in slot 40. The tangs 42A, 42B of these springs are flared outward as they resiliently tend to do, thus digging into the walls of slot 40, such that removal of the springs is essentially impossible without greatly deforming and/or damaging the springs or the base 34. In the fully assembled state, spring arm 30A extends through aperture 38A into recess area 39A and generally adjacent trough 32A, thus capturing tube 29 and urging it into trough 32A.

An examination of FIG. 9 shows that spring 31A for example has a first bend 46 between arm 30A and front wall 44, a second bend 47 between the front and rear walls 44, 43, and a third bend 48 between the rear wall 44 and the anchor 41. When the device is assembled and the mating springs are inserted to the final positions shown. Movement of arm 30A away from trough 32A to allow insertion of tube 29 may flex bend 46 and/or bend 47, while anchor 41A and bend 48 remain essentially fixed. The two anchors of springs 31A and 31B bear hard against each other since they are jammed tightly in slot 40. Consequently flexing one arm 30A for example does not cause the base to correspondingly bend away to relieve the applied force as occurred in the prior art device with a single spring disclosed in the co-pending U.S. patent application having Ser. No. 001,757. In devices of this type the force "applied" by a spring arm depended partially upon the strength of the spring of course, and substantially upon the stiffness of the base to resist the spring. In order for the engagement of the spring and tube to be effective, the base had to be relatively stiff and thus the objective of providing a very soft base for maximum comfort on the patient's face had to be substantially compromised.

In the new invention anchor 41A of spring 31A bears against the anchor 41B of spring 31B; thus the spring force of arm 30A against its trough is a result of both springs opposing each other via their contacting anchors. In this new device the base may have almost any degree of softness, since one spring works against the other spring.

Details of the new spring system are apparent in FIG. 9, where the arrow 49 indicates the direction of pivotal movement of arm 30A toward its anchor part 41A. When arm 30A is deflected the reaction of spring 31A is to urge its anchor part 41A in the same direction; however such tendency is stopped by the wall of slot 40 and by the remaining anchor 41B which essentially cannot move laterally i.e. toward its own arm 30B, because of the remaining wall of slot 40 and because of the spring configuration wherein rear wall 43B of spring 31B is highly resistant to bending.

The tube is held by the force of one spring bearing upon the other in part, and by the spring arm urging the tube into trough area, where the trough and tube are sandwiched between the spring arm 31A and the spring's front wall 44. Thus the force of the spring arm urging the tube against the trough is directly ultimately toward the spring's own front wall 44, thereby compressing the tube and the encompassed portion 34A of the base. Because of the new spring configuration as defined in combination with the new base configuration, there is no tendency of the spring to bend the base or the adjacent wing parts. The device is in effect a balanced system.

For convenience we will give certain arbitrary designations for additional structural parts of this preferred device: the trough 32A is a bearing surface on a support section of the base; said spring arm 30A, when moved to provide for entry of the tube induces a pivoting couple in the whole spring; and between the spring's anchor and arm parts is a transverse central part formed of front and rear panels with an included U-bend, all being a continuous strip.

An additional advantage of the new device is that the spring configuration of three bends with long sections between bends allows for substantially large deflections without overstressing the springs. This is important during use and during assembly where considerable manipulation is required to maneuver each spring into its final position.

As shown in the figures, the left side trough contains a large diameter tube segment representing an NG tube of size French 12 or 14, and the right side trough contains a small diameter tube segment representing an NG tube of size French 16 or 18. It should be apparent that regardless of the tube size, the arms 30A, 30B of the springs will resiliently bend toward and against each tube, urging it tightly against the trough. The geometry and orientation of the trough will position and align the tube properly; the normal force of the spring will produce high frictional resistance against any sliding, i.e. axial or rolling movement of the tube relative to the trough. As discussed above, this friction will be even greater if the tube and device or trough surface are made generally of the same polyvinylchloride. The projections 45 will bite into the outer surface of the tube and add to the overall holding action of this tube-engaging means, without causing any significant damage to the tube beyond surface scratches.

The springs are preferably made of stainless steel, so that they will have the necessary properties of resilience, while being free from rust or tarnish. The springs are shown to be flat strip stock, but preferably they are formed from rolled metal so that all exposed side edges will be rounded and smooth. The curled tips 33A, 33B of the springs function as convenient handles for the surgeon or nurse to grip and squeeze toward each other in order to expose the trough to receive a portion of an NG tube. This curled aspect also prevents the end edge of the spring arms from scratching or snagging anything.

The base portion 34 of this new device has two stepped areas or notches 50, 51 on each side which allow the wing parts 35 to bend around a patient's cheeks without tending to bend or move the base 34 which might alter the accurate placement and alignment of the NG tube relative to the patient's nostril. These notches thus render the side parts of the base very flexible while the central part remains sufficiently firm with the spring to securely hold the NG tube.

FIG. 7 shows a connection 52 at the edge of each wing 35 for connection to a harness as suggested in FIG. 6. There are obviously many alternatives for the end of the harness to be attached to the wing, including heat-sealing, cementing, stapling, etc. There are also many variations of harness designs, so that, the NG stabilizer 28 will be secured from movement up, down, sideways, or forward away from the face. Strap adjustment to provide releasable variation in girth and tightness can be provided by a choice of coupling means.

The new device as described for stabilizing a naso-gastric tube may be equally effective with other indwelling tubes which exit the nose such as but not limited to esophageal, gastric, duodenal, tracheal, pharyngeal, sinusoidal, and naso-pharyngeal tubes. This device furthermore is effective to stabilize an oxygen tube which, though not indwelling, may extend from the area adjacent the upper lip into a nostril; thus a device as shown in FIGS. 7-10 having two aligning, guide areas, can utilize one guide area and gripping means for a naso-gastric tube and other for an oxygen tube. Also the present invention could be used to releasably secure tubes exiting other orifices of the body.

Additional variations are possible wherein the standard tube is replaced with a custom tube especially made for the device. In another case the device and tube are dimensioned to couple exactly, and they are preassembled before packaging. In another case the special tube is arranged to function also as the harness or at least as part of the harness; in this case the proximal part of the tube, after exiting the nostril and being stabilized by the new device, is directed rearward past the patient's cheek to engage with or function as the harness.

The embodiments described above are merely illustrative examples of the invention now defined in the claims following.

What is claimed is:

1. In a naso-gastric tube stabilizer device for engaging an exposed section of a naso-gastric tube extending out of a patient's nostril, the device including:
    a base adapted to lie against the upper lip of a patient and having a central part with a bearing surface thereon,
    spring means secured on said base for releasably urging said tube section against said bearing surface, and
    connection means coupled to said base for releasably engaging said base to the patient's head and for holding said base such that the spring means and the bearing surface are oriented to secure said tube section in substantial alignment with the nostril of a patient, the improvement wherein said base comprises a support section which includes thereon said bearing surface, and said spring means comprises a body part secured to said base, and an arm part extending from said body part and overlying said bearing surface, said body and arm parts of the spring configured to sandwich between them said support section of the base, whereby resilient force of the arm part applied to said bearing surface or said section of the tube adjacent said bearing surface causes compression of said support section between said arm and body parts without stressing or distorting the remainder of said base.

2. A device according to claim 1 wherein spring means comprises a single continuous strip of material.

3. A device according to claim 2 wherein said base has a front part, opposite ends, and a rear part extending laterally between said ends, said bearing surface faces generally forward, said body part of the spring means comprises an anchor part secured to said base, and a central part intermediate said anchor and arm parts, and wherein said central and arm parts of the spring extend respectively behind and in front of said support section of the base.

4. A device according to claim 3 wherein said central part of the spring comprises rear and front panels connected at two adjacent ends thereof by a U-bend.

5. A device according to claim 3 wherein said anchor part penetrates said rear part and extends forwardly therein.

6. A device according to claim 4, wherein said spring means comprises a continuous resilient strip defining said anchor part at one end, then said rear and front panels of said central part defining said U-bend, and then said arm part defining a second bend with said front panel.

7. A device according to claim 6 wherein said anchor defines an approximately 90° bend with said central part, and said arm defines an approximately 135° bend with said central part's front panel.

8. A device according to claims 1 or 2 wherein said spring body part comprises an anchor part that is secured to said base and a central part intermediate said anchor part and said arm part, and wherein said central and arm parts are configured to sandwich between them said support section of said base.

9. A device according to claim 8 wherein said base includes a pair of bearing surfaces which diverge as they descend, each of said surfaces being on a support section of said base, and a pair of said spring means positioned with their arm parts in mutual bearing contact and together secured in said base, each of said arm parts being movable between a first position closely adjacent a bearing surface and a second position spaced apart therefrom to receive said tube section therebetween, said movement to said second position inducing a twisting couple in said spring means, which couple is resisted by the bearing engagement of the anchors of said two spring means.

10. In a naso-gastric tube stabilizer device for engaging an exposed section of a naso-gastric tube extending out of a patient's nostril, the device including:
- a base adapted to lie against the upper lip of a patient and having a central part with a pair of bearing surfaces thereon,
- spring means on said base for releasably urging said tube section against one of said bearing surfaces, and
- connection means coupled to said base for releasably engaging said base to the patient's head and for holding said base such that the spring means and the bearing surfaces are oriented to secure said tube section in substantial alignment with the nostril of a patient, the improvement wherein said central part of the base has rear and front portions with said bearing surfaces being generally on said front portions, and wherein said spring means comprises a pair of similar spring members, each having an anchor with an arm extending from said anchor, said spring members positioned with their anchors adjacent and engaging each other, their arms each adjacent one of said bearing surfaces, and their anchors extending in the direction from rear to front in and secured to said central part, each of said arms resiliently movable between a first position closely adjacent one of said bearing surfaces and a second position spaced apart therefrom, said spring members being configured such that movement of the arms of a first of said spring members between its first and second positions induces a couple or pivoting force in said first spring member which is resisted by said second spring member due to the bearing contact of their anchors.

* * * * *

UNITED STATES PATENT AND TRADEMARK OFFICE
CERTIFICATE OF CORRECTION

PATENT NO. : 4,284,076
DATED : August 18, 1981
INVENTOR(S) : RICHARD HALL

It is certified that error appears in the above—identified patent and that said Letters Patent is hereby corrected as shown below:

Column 4, line 41, omit "This" and insert --The--.

Column 5, line 48 and 49, omit "whereever" and insert --wherever--.

Column 6, line 43, omit "releasable" and insert --releasably--.

Column 7, line 5, after "discovered" insert --however--.

Column 7, line 52, omit "and" second occurrence.

Column 8, line 27, omit "directly" and insert --directed--.

Signed and Sealed this

Seventh Day of June 1983

[SEAL]

Attest:

DONALD J. QUIGG

Attesting Officer

Acting Commissioner of Patents and Trademarks